United States Patent [19]

Goddard

[11] Patent Number: 4,716,231

[45] Date of Patent: Dec. 29, 1987

[54] CHLORINATION OF 2-METHOXYNICOTINIC ACID

[75] Inventor: Carl J. Goddard, Croton, Conn.

[73] Assignee: Pfizer Inc., New York, N.Y.

[21] Appl. No.: 43,056

[22] Filed: Apr. 27, 1987

[51] Int. Cl.$^4$ ................. C07D 213/80; C07D 213/803
[52] U.S. Cl. ..................................... 546/298; 546/345
[58] Field of Search ............................... 546/298, 345

[56] References Cited

U.S. PATENT DOCUMENTS

| | | | |
|---|---|---|---|
| 1,832,484 | 11/1931 | Grether | 568/746 |
| 2,365,981 | 12/1944 | Tindall | 560/946 |
| 3,879,403 | 4/1975 | Kuhla et al. | 546/292 |

*Primary Examiner*—Alan L. Rotman
*Assistant Examiner*—Zinna Northington
*Attorney, Agent, or Firm*—Peter C. Richardson; Lawrence C. Akers

[57] ABSTRACT

A novel process for chlorinating 2-methoxynicotinic acid at the 5-position of the molecule is disclosed. The process involves the use of an alkali metal hypochlorite as the chlorinating agent in a homogeneous aqueous solvent system. The compound so produced, 5-chloro-2-methoxynicotinic acid, is known to be useful as an intermediate leading to various oral hypoglycemic agents of the benzenesulfonylurea class.

6 Claims, No Drawings

CHLORINATION OF 2-METHOXYNICOTINIC ACID

BACKGROUND OF THE INVENTION

This invention relates to a new and useful method of chlorination in the field of pyridine chemistry, leading to an intermediate of known value in the synthesis of various sulfonylurea hypoglycemic agents. More particularly, it is concerned with a novel process for preparing 5-chloro-2-methoxynicotinic acid by chlorinating 2-methoxynicotinic acid at the 5-position of the molecule, thereby obtaining an intermediate known to be of value in the production of certain benzenesulfonylurea oral hypoglycemic agents.

In the past, 5-chloro-2-methoxynicotinic acid has been obtained by chlorinating 2-methoxynicotinic acid with chlorine per se in accordance with the method described by D. E. Kuhla et al. in U.S. Pat. No. 3,879,403. However, this method involves the use of chlorine gas with its associated potential hazards and the use of an aqueous solvent system which leads to heterogeneous reaction conditions with its attendant disadvantages. In the search for newer and more improved methods of production in this particular area, little is known about the use of other chlorinating agents with the pyridine ring system, even though these agents have been employed with variable success in the field of non-heterocyclic chemistry. For instance, alkali metal hypochlorite solutions have been used in the past to chlorinate nitroparaffins within a certain restricted pH range (e.g., pH 10-14) according to the method described by J. B. Tindall in U.S. Pat. No. 2,365,981, while similar solutions have also been employed in the chlorination of p-hydroxybiphenyl to give 3-chloro-4-hydroxybiphenyl according to the method of described.by E. F. Grether in U.S. Pat. No. 1,832,484.

SUMMARY OF THE INVENTION

In accordance with the present invention, it has now been found possible to selectively chlorinate 2-methoxynicotinic acid at the 5-position of the molecule and so obtain 5-chloro-2-methoxynicotinic acid in pure form and in high yield by the use of an alkali metal hypochlorite as the chlorinating agent in an aqueous solvent system More particularly, the novel process of the invention involves subjecting 2-methoxynicotinic acid to the chlorinating activity of an alkali metal hypochlorite in a homogeneous aqueous solvent system at a temperature that is in the range of from about 10° C. up to about 30° C. until said chlorination reaction is substantially complete. In this way, 2-methoxynicotinic is readily converted to 5-chloro-2-methoxynicotinic acid in a most facile manner without the previously discussed disadvantages connected with the use of gaseous chlorine.

DETAILED DESCRIPTION OF THE INVENTION

In accordance with the process of this invention, the ratio of the 2-methoxynicotinic acid starting material to the alkali metal hypochlorite reagent employed as the chlorinating agent is usually in the range of from about 1.0:1.0 to about 1.0:6.0, with the preferred range being from about 1.0:1.2 to about 1.0:2.0, in order to effect the desired chlorination at the 5-position of the molecule. The process is normally carried out by contacting the 2-methoxynicotinic acid substrate and the alkali metal hypochlorite reagent in a homogeneous aqueous solvent system at a temperature that is in the previously indicated range of ca. 10°-30° C. until the chlorination reaction effecting conversion to 5-chloro-2-methoxynicotinic acid is substantially complete. Preferred reaction conditions for these purposes include conducting the reaction at or near room temperature for a period of at least about 16 hours. Although any alkali metal hypochlorite such as lithium, sodium or potassium hypochlorite can be employed in the process, the preferred reagent is sodium hypochlorite. Consequently, it has been found most convenient to carry out the reaction in a dilute aqueous sodium hypochlorite solution, for example 5.25% aqueous sodium hypochlorite, which is commercially available under the trademark name of Clorox. Upon completion of the reaction, the desired product, viz., 5-chloro-2-methoxynicotinic acid, is readily recovered from the reaction mixture by simple acidification and filtration, or by acidification and extraction with a suitable solvent such as chloroform, followed by further purification, if necessary, via trituration with an appropriate solvent normally used for these purposes (e.g., hexane).

As previously indicated, 5-chloro-2-methoxynicotinic acid, the product afforded by the process of this invention, is a known compound that serves as a valuable intermediate that ultimately leads to certain benzenesulfonylurea oral hypoglycemic agents which are described and claimed by D. E. Kuhla et al. in U.S. Pat. No. 3,879,403. More specifically, 5-chloro-2-methoxynicotinic is first converted to 5-chloro-2-methoxynicotinoyl chloride and then to 4-[2-(5-chloro-2-methoxynicotinamido)ethyl]benzenesulfonamide prior to ultimately yielding either 1-cyclohexyl-3-{4-[2-(5-chloro-2-methoxynicotinamido)ethyl]benzenesulfonyl}urea or 1-(bicyclo[2.2.1]hept-5-en-2-yl-endo-methyl)3-{4-[2-(5-chloro-2-methoxynicotinamido)ethyl]benzenesulfonyl}urea or 1-(4-chlorocyclohexyl)-3-{4-[2-(5-chloro-2-methoxynicotinamido)ethyl]benzenesulfonyl}urea by the multi-step method of the prior art process earlier described by D. E. Kuhla et al. in the aforesaid U.S patent.

Hence, the novel process of the present invention now provides the valuable intermediate known as 5-chloro-2-methoxynicotinic acid in pure form and in high yield by a unique one-step selective chlorination method, which represents a major improvement over the prior art in view of the ease of synthesis and greatly reduced nature of the costs involved. More specifically, it circumvents the use of chlorine gas and its associated hazards and allows the reaction to proceed under normally homogeneous reaction conditions, thereby avoiding bulky and cumbersome suspensions.

PREPARATION A

A stirred slurry consisting of 35 g. (0.22 mole) of 2-chloronicotinic acid (available from Lonza Inc. of Fair Lawn, N.J.) in 400 ml. of methanol was treated with 25.4 g. (0.47 mole) of sodium methylate, which was added thereto in a portionwise manner. Stirring was then continued until a clear solution was obtained. At this point, the liquid reaction mixture was transferred to a steel autoclave and heated at 125° C. for a period approximately 16 hours (i.e., overnight). Upon completion of this step, the resulting reaction mixture was cooled to room temperature (~20° C.), filtered and the filter cake thus obtained was washed with methanol.

The combined organic filtrate and methanol washings were then concentrated in vacuo to give a white solid material, which was subsequently dissolved in water. The latter aqueous solution was then adjusted to pH 3.0 with the aid of 6N hydrochloric acid and immediately filtered to remove (i.e., recover) the precipitated solid product, which was thereafter air-dried to constant weight for a period of approximately 16 hours (i.e., overnight). In this manner, there were ultimately obtained 21.8 g. (64%) of pure 2-methoxynicotinic acid, m.p. 147°-148° C. (literature m.p. 144°-146° C., according to D. E. Kuhla et al., in U.S. Pat. No. 3,879,403). The pure product was further characterized by means of nuclear magnetic resonance data.

EXAMPLE 1

A 306 mg. (0.002 mole) sample of 2-methoxynicotinic acid (the product of Preparation A) was added in one portion to 20 ml. of well-stirred 5.25% aqueous sodium hypochlorite solution (Clorox). The resulting mixture (now a solution) was then allowed to stir at room temperature ($\sim$20° C.) for a period of approximately 18 hours (i.e., overnight). Upon completion of this step, the reaction mixture was acidified with 10 ml. of 1N hydrochloric acid and the resulting precipitate was subsequently extracted with chloroform. The organic extracts were then combined, dried over anhydrous magnesium sulfate and filtered, and the resulting filtrate was subsequently concentrated in vacuo to afford 195 mg. (52%) of pure 5-chloro-2-methoxynicotinic acid, m.p. 139°-141° C. (literature m.p. 149°-150° C., according to D. E. Kuhla et al. in U.S. Pat. No. 3,879,403). The pure product was further characterized by means of nuclear magnetic resonance data and mass spectroscopy.

EXAMPLE 2

A 217 g. (1.42 mole) sample of 2-methoxynicotinic acid (the product of Preparation A) was added portionwise to 2.5 liters of well-stirred 5.25% aqueous sodium hypochlorite solution (Clorox) at 10° C., with sufficient cooling being maintained throughout the course of the addition step to keep the temperature of the reaction mixture below 28° C. Upon completion of this step, the resulting reaction mixture was allowed to stir at room temperature ($\sim$20° C.) for a period of approximately 16 hours (i.e., overnight) and then acidified to pH 2.0 with concentrated hydrochloric acid. The precipitated solid product was then collected by means of suction filtration and thereafter triturated with two-500 ml. portions of hexane, followed by drying under a high vacuum to ultimately yield 201 g. (75%) of pure 5-chloro-2-methoxynicotinic acid. This product was identical in every respect with the product of Example 1, as particularly attested to by nuclear magnetic resonance data.

EXAMPLE 3

In a 22-liter three-necked, round-bottomed reaction flask equipped with thermometer, mechanical stirrer and vent, there were placed 12 liters of 5.25% aqueous sodium hypochlorite solution (Clorox) at 10° C. Stirring was commenced and 868 g. (5.66 mole) of 2-methoxynicotinic acid were added portionwise to the stirred solution over a period of 75 minutes, with sufficient cooling being maintained throughout the course of the addition step to keep the temperature of the reaction mixture below 30° C. Upon completion of this step, the resultant white slurry at 21° C. was treated with an additional 4 liters of fresh 5.25% aqueous sodium hypochlorite (Clorox) to bring the pH of the reaction mixture to about pH 7.0. The latter mixture was thereafter stirred at ambient temperature for a period of approximately 18 hours. The tan slurry which resulted was then treated with 1 gal. of chloroform and the pH was adjusted to a value of pH $\sim$1.5 by the addition of concentrated hydrochloric acid, followed by further dilution with 1.5 gal. of chloroform. The separated chloroform layer was then filtered and saved, while the aqueous layer was extracted with 1 gal. of fresh chloroform. The combined organic layers were then washed once with 4 liters of 10% aqueous hydrochloric acid and dried over anhydrous magnesium sulfate. After removal of the drying agent by means of filtration and the solvent by means of evaporation under reduced pressure, there was obtained a yellow-white solid that was subsequently triturated with 3 liters of hexane and then filtered. The resulting off-white solid was then washed with 1 liter of fresh hexane on the filter funnel and airdried to constant weight for a period of approximately 16 hours to ultimately afford 782.4 g. (73%) of pure 5-chloro-2-methoxynicotinic acid, m.p. 137°-138° C. This product was identical in every respect with the product of Example 1, as particularly attested to by nuclear magnetic resonance data.

I claim:

1. A process for chlorinating 2-methoxynicotinic acid at the 5-position of the molecule, which comprises subjecting said acid to the chlorinating activity of an alkali metal hypochlorite in a homogeneous aqueous solvent system at a temperature that is in the range of from about 10° C. up to about 30° C. until said chlorination reaction is substantially complete.

2. A process as claimed in claim 1 wherein the alkali metal hypochlorite employed as reagent is sodium hypochlorite.

3. A process as claimed in claim 1 wherein the molar ratio of the 2-methoxynicotinic acid starting material to the sodium hypochlorite reagent is in the range of from about 1.0:1.0 to about 1.0:6.0.

4. A process as claimed in claim 3 wherein said molar ratio is in the range of from about 1.0:1.2 to about 1.0:2.0.

5. A process as claimed in claim 1 wherein the reaction is conducted at room temperature for a period of at least about 16 hours.

6. A process as claimed in claim 1 wherein the 5-chloro-2-methoxynicotinic acid so produced is recovered from the reaction mixture.

* * * * *